US00PP14535P39

(12) United States Plant Patent
Lopez

(10) Patent No.: US PP14,535 P3
(45) Date of Patent: Feb. 17, 2004

(54) PEACH TREE NAMED 'PLAPIOMEL'

(50) Latin Name: *Prunus persica*
Varietal Denomination: Plapiomel

(75) Inventor: José Miguel Arias Lopez, Tudela (ES)

(73) Assignee: Plantas de Navarra, S.A. (ES)

( * ) Notice: Subject to any disclaimer, the term of this patent is extended or adjusted under 35 U.S.C. 154(b) by 0 days.

(21) Appl. No.: 10/185,662

(22) Filed: Jun. 27, 2002

(65) Prior Publication Data

US 2003/0079262 P1 Apr. 24, 2003

(30) Foreign Application Priority Data

Oct. 23, 2001 (EP) ..... 2001/1661

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new and distinct variety of Peach tree characterized by its low chilling requirement, early to mid-season ripening, having attractive clingstone fruit having yellow fleshed, medium-high firm, good quality fruit.

3 Drawing Sheets

Classification: The present invention relates to a new *Prunus persica* (L.) Batsch—Peach.

Variety denomination: The new plant has the varietal denomination 'Plapiomel'.

BACKGROUND OF THE INVENTION

The new variety of Peach tree was created in a breeding program by crossing two parents; in particular, by crossing as seed parent a variety designated '89-062' (unpatented) and as pollen parent a variety designated '91-002' (unpatented). Both, female and male, are components of a parent collection from a selection made between plants issued from seeds got in a free pollination in a population of different origin done in 1989 and 1991. Both parental varieties are property and have not been commercialized.

The seeds resulting from this controlled hybridization were germinated in a greenhouse in the spring of 1995 and planted in a field on the farm of La Mogalla in Cartaya (Huelva), Spain, 7° W., 37° N., 45 feet elevation. The seedlings fruited during the Spring of 1997, one designated '95.03.003-P,' (unpatented) was selected for its low chilling requirement (250 to 300 hours) early to mid-season ripening, attractive fruit shape and color, yellow flesh, medium-high firm fruit, and good fruit quality. During 1998, the original plant selection was propagated asexually, at the above noted location, by budding onto standard Peach rootstock variety designated 'GF-677' (non patented) and a test plot of 4 plants was established.

The new variety has been asexually multiplied several times since 1999 at this location by budding onto the standard Peach rootstock variety designated as 'GF-677' (unpatented) and no incompatibility with Peach rootstock has occurred following budding. During all asexual reproduction, the characteristics of the original plant have been maintained and no aberrant phenotypes have appeared.

SUMMARY OF THE INVENTION

The new Peach tree variety differs from its parents and other known cultivars of Peach Trees by producing clingstone fruits with a low chilling requirement (250 to 300 hours) and an early to mid-season ripening date. The fruits of the new variety are ripe for commercial harvesting and shipment between approximately May 30$^{th}$ to May 15$^{th}$. These harvesting dates are approximately 25 days earlier than the harvest dates of the commercial Peach variety 'Vista' (U.S. Plant Pat. No. 9,549), approximately 13 days earlier than the harvest dates of the commercial Peach variety 'Redhaven' (unpatented), approximately 15 days earlier than the harvest dates of the commercial peach variety 'Rich Lady' (U.S. Plant Pat. No. 7,290), and approximately 20 days later than the harvest dates of the commercial peach variety 'Rich May' (U.S. Plant Pat. No. 7,432).

COMPARISON WITH OTHER VARIETIES

'Plapiomel' differs from Peach trees of 'Vista,' 'Rich May' and 'Rich Lady' by its lower chilling requirement (200 to 300 hours); whereas 'Vista' has a 700 to 800 hour chilling requirement; 'Rich May' has a 800 to 900 hour chilling requirement; and 'Rich Lady' has a 750 to 850 hour chilling requirement.

'Plapiomel' produces round shaped clingstone fruit with a slightly apical tip; whereas 'Vista' produces semi-freestone fruit with an ovoid shape; 'Rich May' produces more firm, ovoid shaped fruit with a strong apical tip. The fruit of 'Rich Lady' also have an ovoid shape.

The surface of the fruit of the new variety is covered approximately 60% to 80% with a red over a yellow-greenish color; whereas 100% of the fruit surface of 'Rich Lady' shows a red color.

BRIEF DESCRIPTION OF THE DRAWINGS

The accompanying photographic illustrations show typical specimens of the new variety as true to color as is reasonably possible to make in illustrations of this character.

DESCRIPTION OF THE NEW VARIETY

Figure 1:
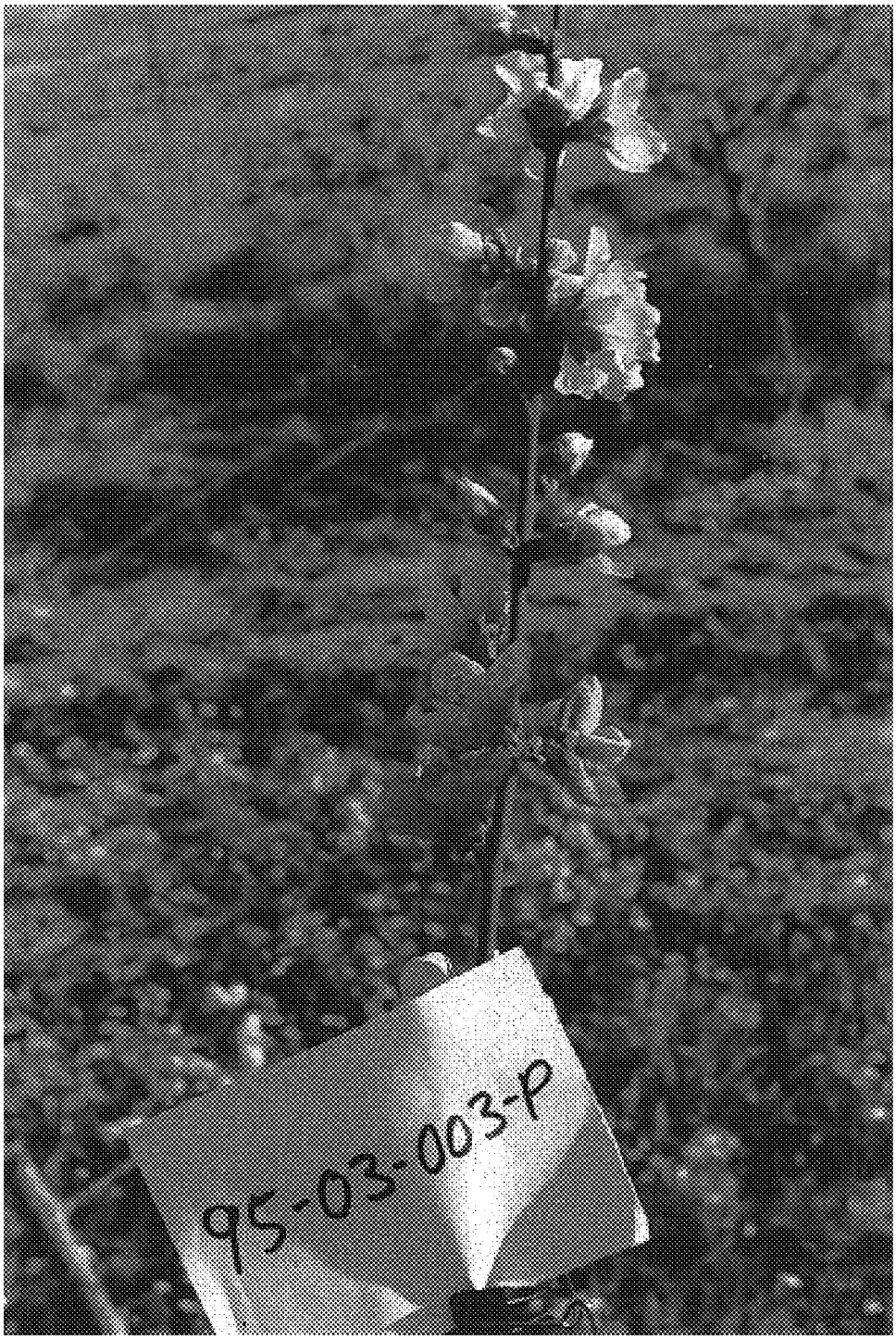
FIG. 1 shows typical flowers of the new variety.
Figure 2:
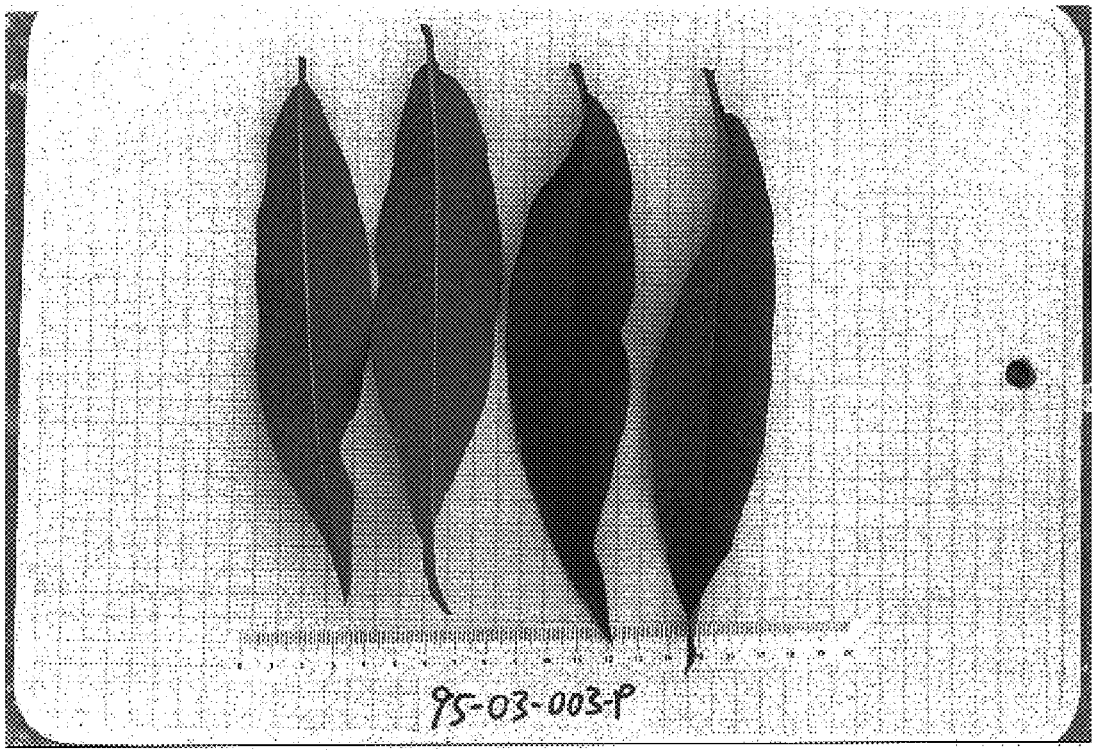
FIG. 2 shows the coloration of the dorsal and ventral leaves of the new variety.
Figure 3:
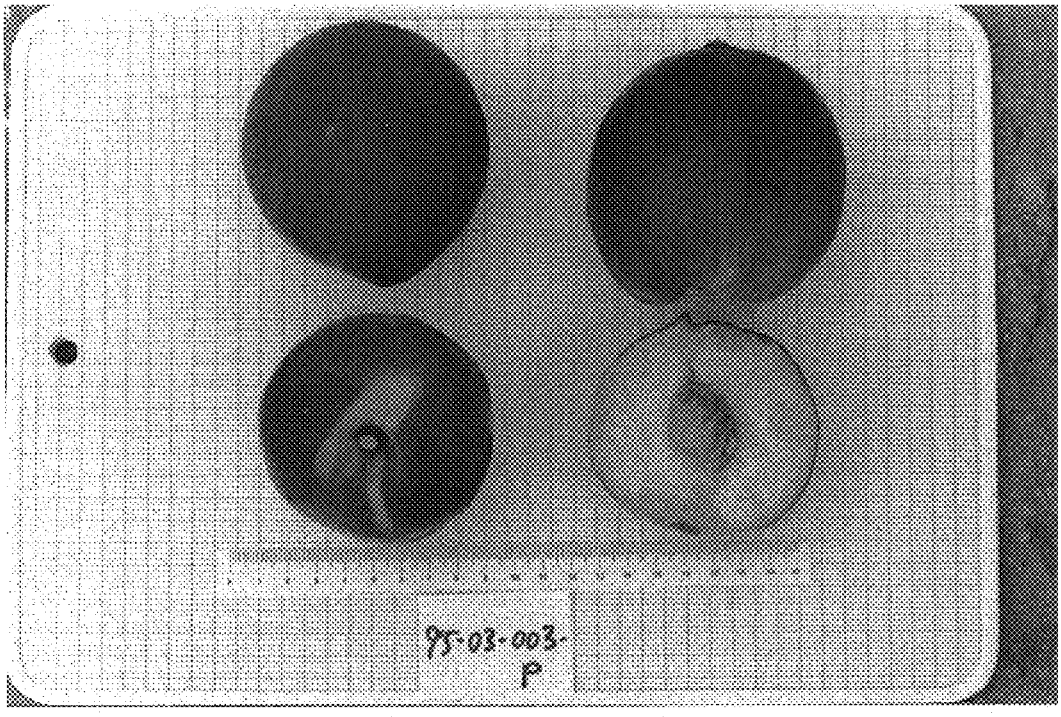
FIG. 3 shows the external coloration of fruits of the new variety when sufficiently matured for harvesting and shipment and one fruit of the new variety dissected in the equatorial plane to illustrate the flesh and stone characteristics.

The following observations and descriptions are of plants grown at the orchard previously described, located near the town of Cartaya, Huelva, Spain. Observations were made of the original seedling tree on its own root during the growing years of 1997 to 2001. Plants described are from seed germinated in Spring of 1995 with the trees planted in a field in December 1995. First fruit was observed in Spring 1997.

In this description, it is to be understood that references of the dimensions, sizes, colors, etc. of the botanical and phonological characteristics of the new variety are approximations of averages set forth as accurately as practical. Phenotypic expression may vary with light intensity and cultural and environmental conditions. The color references used in this description, are to The Royal Horticultural Society Colour Chart (R.H.S.C.C.) and terminology used in the color descriptions herein refers to plate numbers in said color chart.

Tree:

*Size.*—Generally average to above-average as compared to other common Peach cultivars.

*Productivity.*—Approximately 27000 to 29000 Kgrs/Ha.

*Form.*—Considered upright to upright, spreading in form.

*Height.*—Original seedling tree reached approximately 3.2 m at end of 2001 growing season.

*Width.*—Original seedling reached approximately 1.80 m at end of 2001 growing season.

*Current season growth.*—Approximately 0.95 to 1.1 m.

*Regularity of bearing.*—Regular.

Trunk:

*Thickness.*—Approximately 110 mm. Diameter: Approximately 15 cm when measured at a distance above the soil level at end of 2001 growing season.

*Bark texture.*—Considered moderately rough with numerous scarf skin flat oval lenticels present. Color: Grey Group near 201C to 201B.

Branches:

*Size.*—Considered medium for the species.

*Diameter.*—About 65.4 mm when measured during the 3$^{rd}$ year after grafting.

*Surface texture.*—Average. Current Season Shoots: Substantially glabrous. Color: Greyed-green Group near 194B to 195B. Mature Branches: Appearing furrowed on wood which is several years old. Color: Greyed-green Group near 197C to 197B.

Leaf:

*Size.*—Considered average for the species; leaf measurements taken from vigorous upright current season growth at approximately mid-shoot. Length: Approximately 140 to 160 mm. Width: Approximately 38 to 46 mm. Thickness: Approximately 1 to 2 mm.

*Base shape.*—Slightly oblique.

*Form.*—Lanceolate.

*Tip form.*—Acuminate.

*Color.*—Upper Side: Green Group near 146A to 147A. Underside: Yellow-Green Group near 146D to 146B.

*Texture.*—Glabrous.

*Margins.*—Crenate, generally uniform.

*Leaf petiole.*—Considered medium-long. Length: Approximately 10 to 14 mm. Diameter: Approximately 1.5 to 2 mm.

*Leaf glands.*—Reniform; generally 2 to 4 per side. Length: Approximately 1.0 to 1.5 mm. Width: Approximately 0.5 to 1.0 mm.

*Venation.*—Pinnately net veined, mid-vein color near 149D to 150D.

*Sepals.*—Length about 8 mm, width about 5 mm, usually 5 per flower; color near 178A to 181A.

Inflorescence:

*Flower bud.*—Length about 7 mm, diameter about 2 mm, shape ovoid, color near 178B to 177A.

*Flowers.*—Bloom occurs prior to vegetative bud break; generally double individual flowers at a single node; perfect self-fertile. Blooming Time: Considered medium in relation to other Peach cultivars. Date of Bloom: First, February 9$^{st}$; Full, February 16$^{th}$. Flower Diameter: Approximately 41 to 45 mm at full bloom. Bloom Quantity: Considered very abundant.

*Petalage.*—Considered large for the species. Length: Approximately 17 to 19 mm. Width: Approximately 17 to 19 mm. Shape: Rounded.

*Petal count.*—Nearly always 5.

*Texture.*—Glabrous.

*Color.*—Near 69D to 69C; abaxial color of petal near 69D.

*Apex.*—The petal apices appear domed.

*Flower pedicel.*—Length about 3 mm, diameter about 2 mm, color near 144D.

*Stamens.*—Numerous; with pollen present; fertile and abundant.

Reproductive organs:

*Anthers.*—Length about 1 to 1.5 mm, width about 1 mm, color between 185B to 185A.

*Pollen production.*—Pollen is abundant, color between 20B to 20A.

*Filaments.*—Length about 15 mm, color between 62D to 62C, darkening with advanced maturity.

*Pistil.*—Length about 14 mm, including ovary; surface texture pubescent, color near 150D.

Fruit: In firm ripe condition at full commercial maturity, first fruit picked on approximately May 30$^{th}$; last pick of same fruit in 2001 was approximately June 15$^{th}$ in Cartaya, Huelva, Spain conditions.

*Size.*—Generally considered large in size, slightly not uniform. Cheek Diameter: Approximately 70 to 88 mm. Suture Diameter: Approximately 72 to 90 mm. Axial diameter: Average about 76 to 78 mm.

*Form.*—Rounded, slightly flat; generally slightly not-uniform.

*Suture.*—Extending from base to apex, suture appears as a very thin line at same level as skin.

*Stem cavity size.*—Considered small for the species. Width: Approximately 21 to 22 mm. Length: Approximately 28 to 30 mm. Depth: Approximately 16 to 18 mm.

*Form.*—Ovoid.

*Fruit base.*—Slightly concave and uniform.

*Fruit apex.*—Rounded with a slight apical tip.

*Fruit skin.*—Average in thickness. Surface Texture: Very little pubescence. Skin Acidity: Neutral.

*Tenacious to flesh.*—Yes; at commercial maturity.

*Tendency to crack.*—Not observed. Skin Color: Approximately 60% to 80% of fruit surface Red Group near 45B to 46A; not brilliant and about 20% to 40% of surface Yellow-green Group near 145C to 145D.

*Firmness.*—3.5 to 4.5 $Kg/cm^2$=Resistance to penetration measured in Kilograms ($Kg/cm^2$) obtained by Penetrometer ROZE Mod. Arbelette, with a 50 $mm^2$ section head.

*Flesh color.*—Yellow Group near 11B to 11A.

*Flesh fibers.*—Not present throughout flesh at maturity.

*Flesh texture.*—Generally melting.

*Flavor.*—Considered sweet; medium acidic; soluble solids, as °Brix, about 11 to 12.

*Aroma.*—Pleasant and medium.

*Eating quality.*—Very good to excellent; well above average when compared to other common commercial varieties.

*Stone.*—Attachment: Clingstone at full commercial maturity. Stone Size: Large for the species. Length: Approximately 35 to 37 mm. Width: Approximately 25 to 27 mm. Thickness: Approximately 19 to 20 mm. Stone Form: Ovoid-elongated. Stone Color: Yellow-Orange Group near 22A to 26B. Tendency to Split: None observed. Kernel: Form is ovoid-elongated. Length: Approximately 15 to 16 mm;. Width: Approximately 10 to 11 mm.

General: Early to mid-season maturity producing a highly attractive colored, medium-high firm fruit.

Keeping quality: Fruit stored well up to 15 to 20 days after harvest at temperatures of about 1° C.

Resistance to insects and disease: No particular susceptibilities were noted.

Shipping quality: Well above average.

Hardiness: No Winter injury has been noted during years of evaluation in the South of Spain, drought and heat tolerance not known.

The new variety of Peach tree possesses the characteristics described above, as a result of the growing conditions prevailing in Cartaya, Huelva, Spain. It is to be expected that variations in these characteristics may occur when farmed in areas with different climatic conditions, different soil types, and/or varying cultural practices.

I claim:

1. A new and distinct variety of Peach tree substantially as illustrated and described herein.

* * * * *